(12) United States Patent
Wainright et al.

(10) Patent No.: US 6,905,583 B2
(45) Date of Patent: Jun. 14, 2005

(54) CLOSED-LOOP CONTROL OF ELECTROKINETIC PROCESSES IN MICROFLUIDIC DEVICES BASED ON OPTICAL READINGS

(75) Inventors: Ann Wainright, Cupertino, CA (US); Torleif Bjornson, Gilroy, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 24 days.

(21) Appl. No.: 10/731,977

(22) Filed: Dec. 10, 2003

(65) Prior Publication Data

US 2004/0118684 A1 Jun. 24, 2004

Related U.S. Application Data

(60) Provisional application No. 60/433,183, filed on Dec. 13, 2002.

(51) Int. Cl.$^7$ .............................................. G01N 27/447
(52) U.S. Cl. ....................................... 204/453; 204/451
(58) Field of Search ................................ 204/451, 454, 204/453, 452, 601–604

(56) References Cited

U.S. PATENT DOCUMENTS

| | | | | |
|---|---|---|---|---|
| 5,378,334 A | * | 1/1995 | Dadoo et al. ................ | 204/452 |
| 5,599,432 A | | 2/1997 | Manz .......................... | 204/451 |
| 6,391,622 B1 | | 5/2002 | Knapp ....................... | 435/285.2 |
| 6,685,813 B2 | | 2/2004 | Williams ..................... | 204/549 |
| 2002/0008029 A1 | | 1/2002 | Williams ..................... | 204/453 |
| 2002/0079223 A1 | * | 6/2002 | Williams et al. ............. | 204/549 |
| 2002/0189946 A1 | * | 12/2002 | Wainright et al. ........... | 204/453 |
| 2004/0060821 A1 | | 4/2004 | Williams ..................... | 204/549 |

FOREIGN PATENT DOCUMENTS

| | | | | |
|---|---|---|---|---|
| EP | 1162455 A1 | * | 12/2001 | ......... G01N/27/447 |
| WO | WO 92/13229 A2 | * | 8/1992 | ......... G01N/27/447 |

OTHER PUBLICATIONS

Bodor et al., "Isotachophoresis and isotachophoresis—zone electrophoresis separations of inorganic anions present in water samples on a planar chip with column–coupling separation channels and conductivity detection", Journal of Chromatography A, 916 (2001) 155–165.

Burgi et al., "On–Line Sample Preconcentration for Capillary Electrophoresis", Handbook of Capillary Electrophoresis, pp. 479–527, 1997.

Jacobson et al., "Microchip electrophoresis with sample stacking", Electrophoresis, 1995, 16, pp. 481–486.

Kaniansky et al., "Capillary Electrophoresis Separation on a Planar Chip with the Column–Coupling Configuration of the Separation Channels", Anal. Chem. 2000, 72, 3596–3604.

Křivánková et al., "Isotachophoresis in zone electrophoresis", Journal of Chromatography A, 838 (1999) pp. 55–70.

Stegehuis et al., "Analyte focusing in capillary electrophoresis using on–line isotachophoresis", Journal of Chromatography, 591 (1992) pp. 341–349.

Wanders et al., "Isotachophoresis in Capillary Electrophoresis", CRC Handbook of Capillary Electrophoresis: A Practical Approach, pp. 112–127, 1994.

* cited by examiner

Primary Examiner—Alex Noguerola
(74) Attorney, Agent, or Firm—Stephen C. Macevicz

(57) ABSTRACT

A method for performing an electrophoretic separation on a microfluidic device includes applying an electric field to electrokinetically move a sample along a channel towards a location. The sample may be concentrated by application of the electric field. The method further comprises optically monitoring the location for at least a portion of the sample. Once the sample is detected, the electric field is automatically changed to further manipulate the sample. The sample may be spatially separated along a separation channel or channel portion. The closed-loop control of electric fields may be performed using a control unit adapted to apply a voltage potential between electrodes and an optical detector such as an LIF detector.

19 Claims, 8 Drawing Sheets

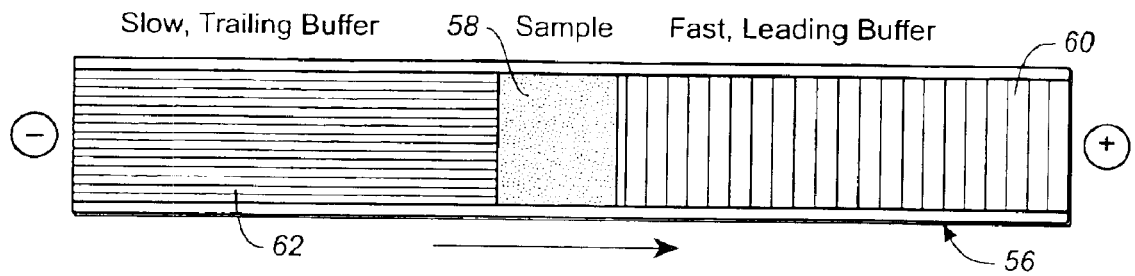
FIG._1A
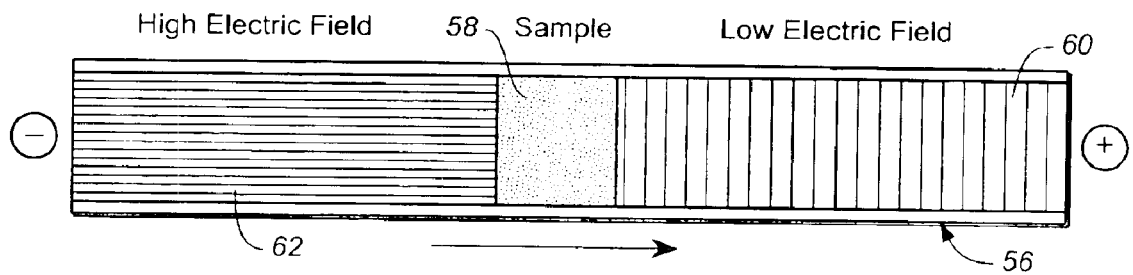
FIG._1B
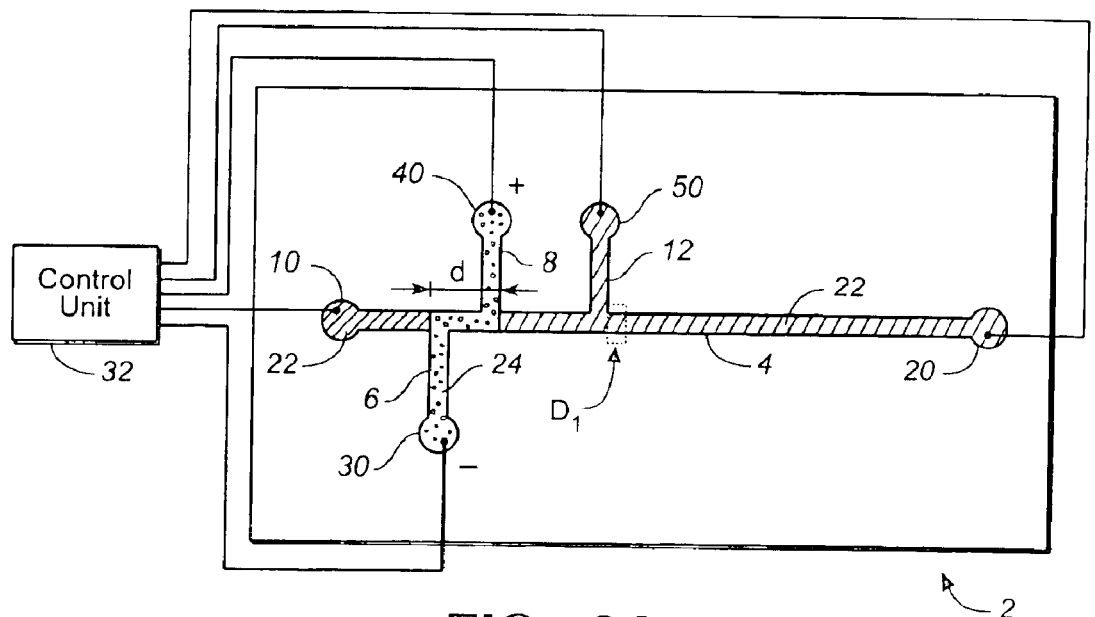
FIG._2A

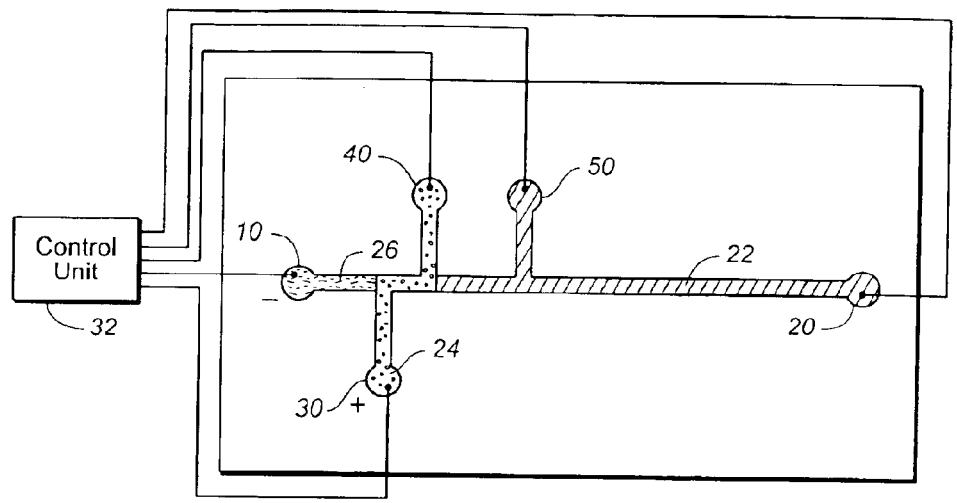
FIG._2B
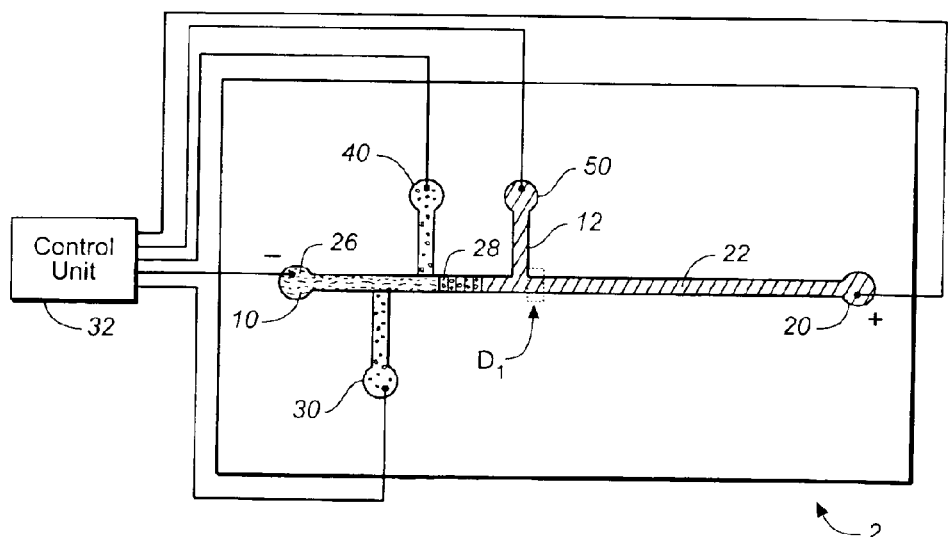
FIG._2C

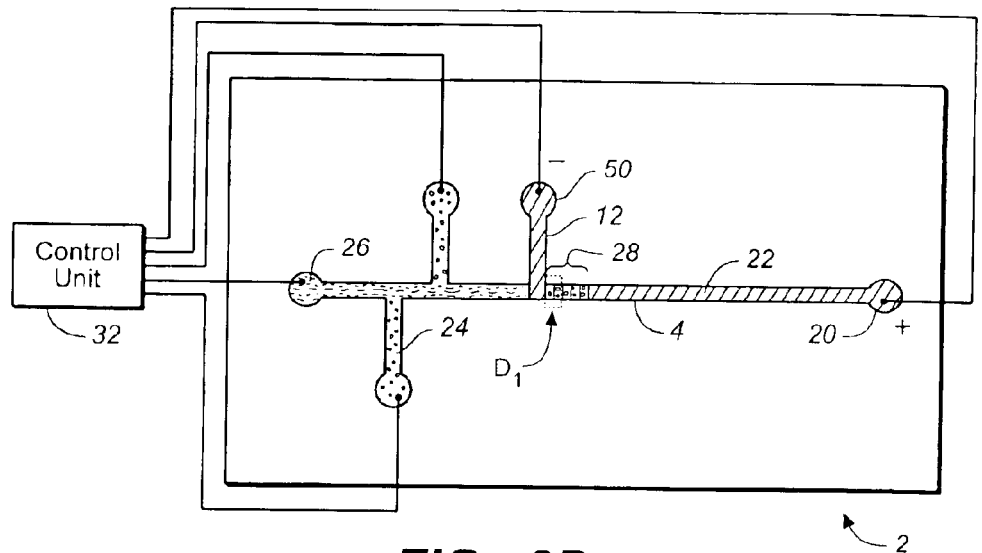
FIG._2D
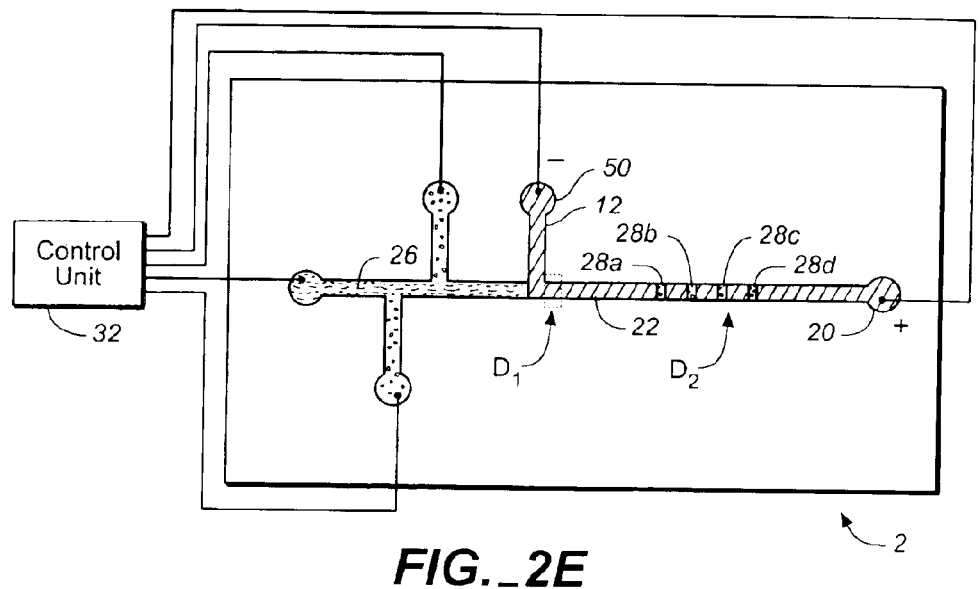
FIG._2E

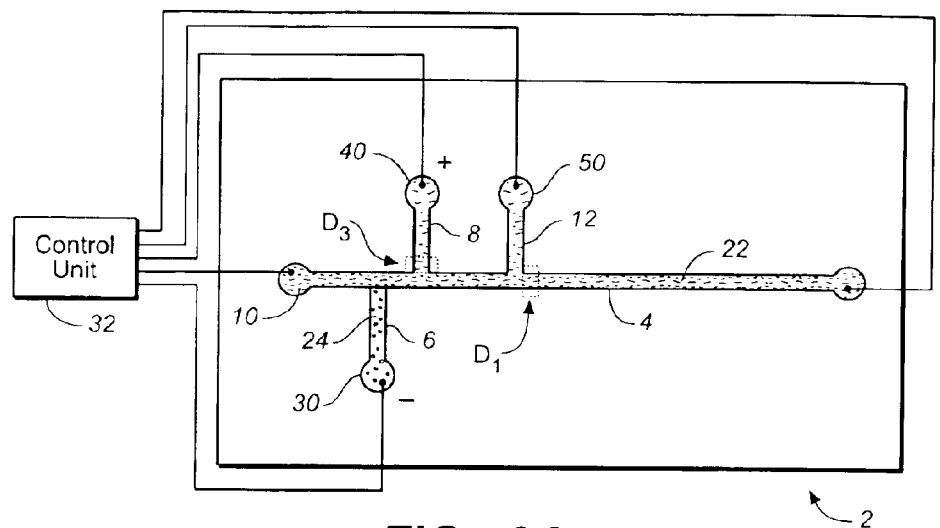
FIG._3A
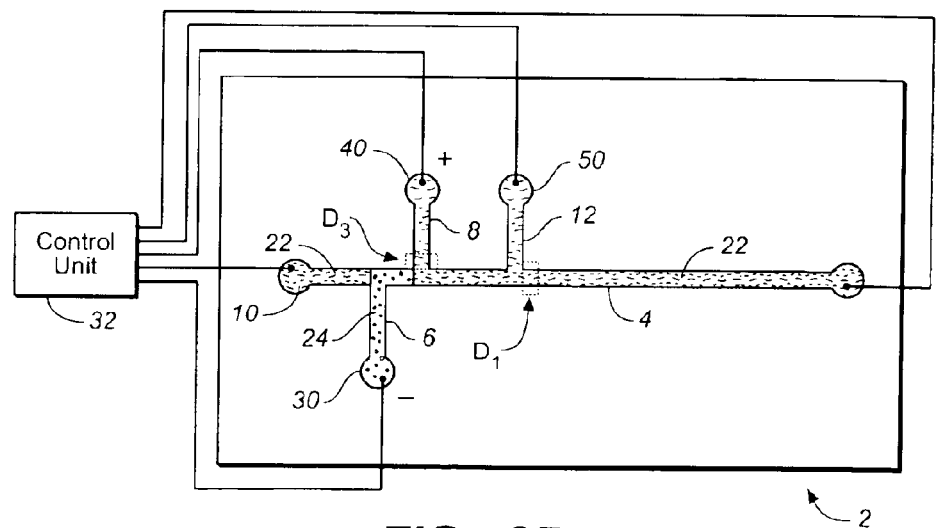
FIG._3B

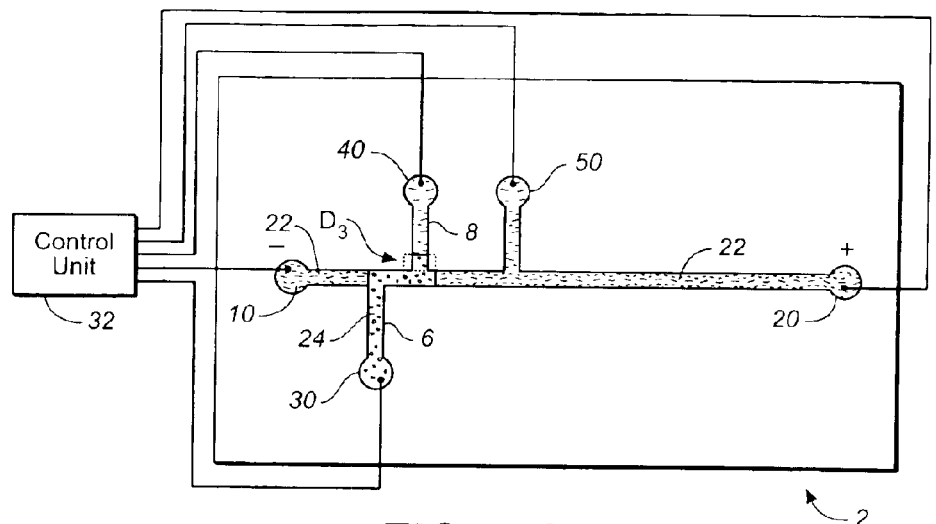
FIG._3C
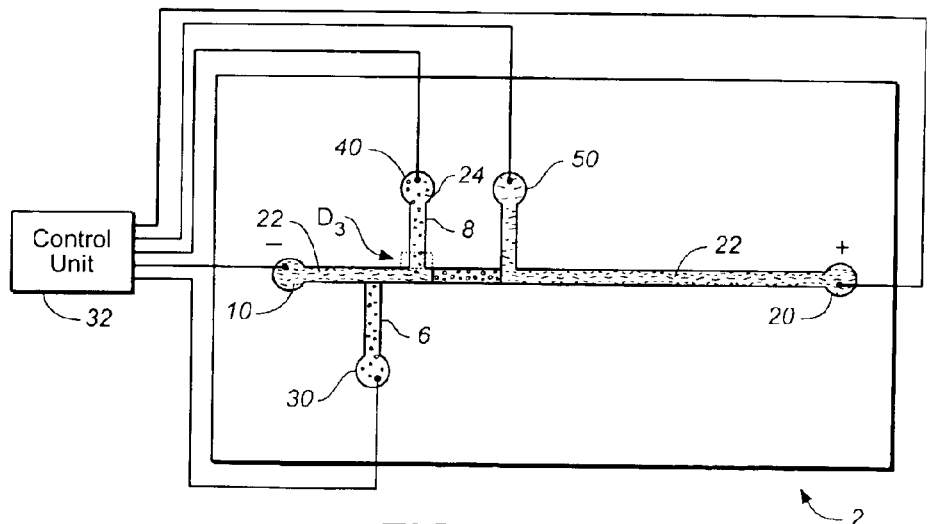
FIG._3D

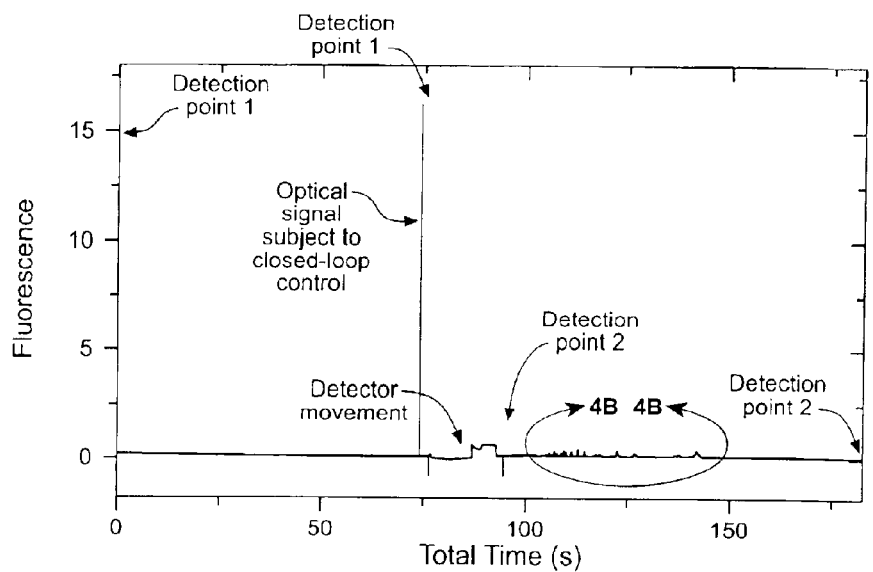
FIG._4A
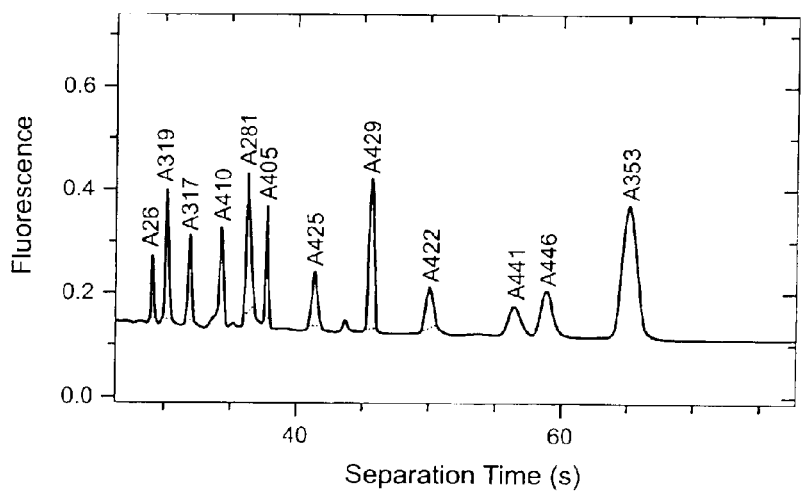
FIG._4B

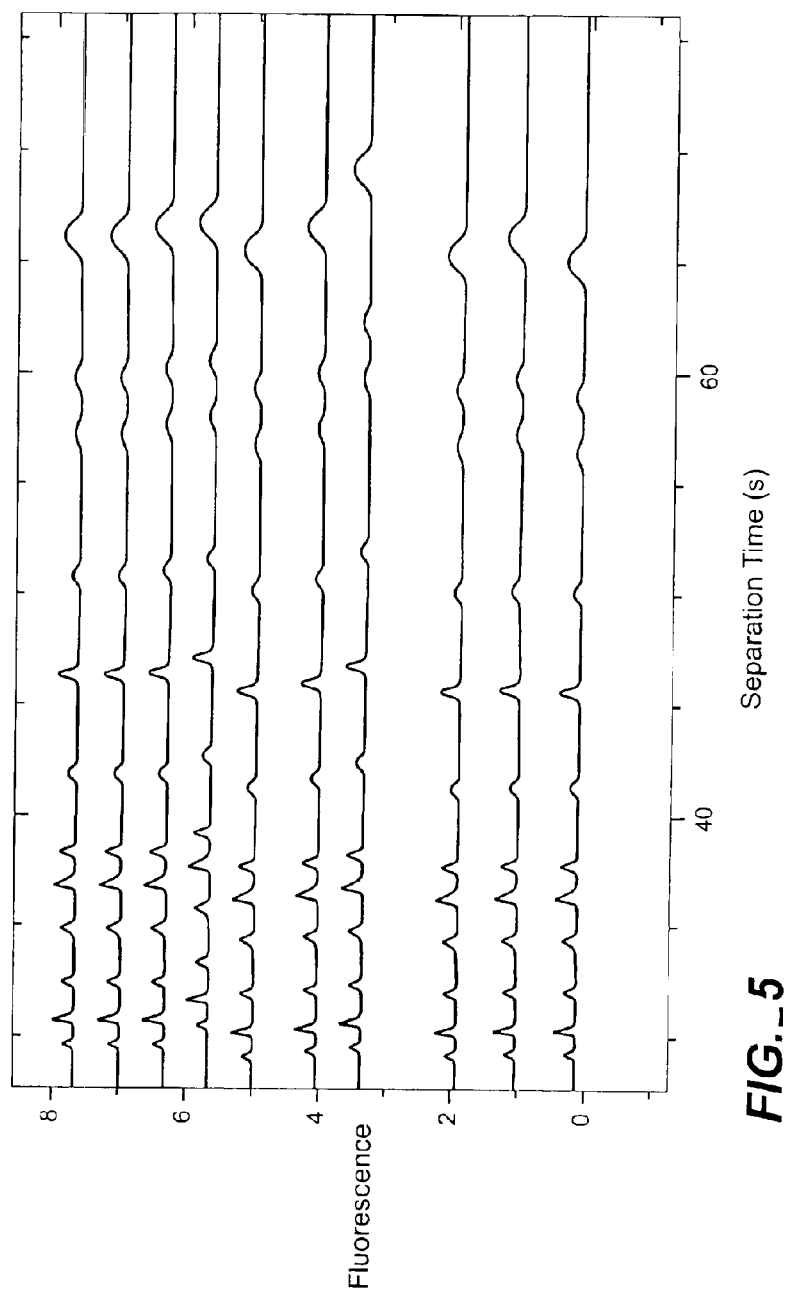
FIG._5

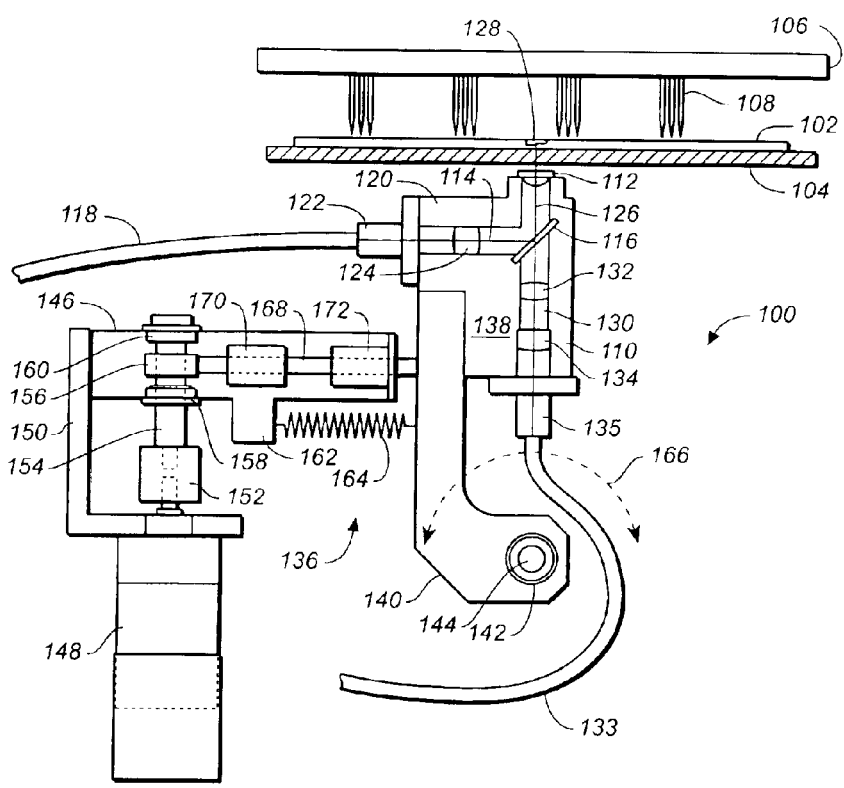
FIG._6

CLOSED-LOOP CONTROL OF ELECTROKINETIC PROCESSES IN MICROFLUIDIC DEVICES BASED ON OPTICAL READINGS

CROSS-REFERENCE TO RELATED APPLICATIONS AND PATENTS

This application claims priority from U.S. provisional applications Ser. No. 60/433,183, filed 13 Dec. 2002, which application is incorporated herein by reference in its entirety

FIELD OF THE INVENTION

The present invention is directed to electrokinetic processes performed on microfluidic devices and in particular, to automatically controlling electric fields used in carrying out electrophoretic separations.

BACKGROUND ART

Microfluidics is revolutionizing the way activities are performed in a substantial proportion of chemical and physical operations. One area of microfluidics is the manipulation of small volumes of liquids or liquid compositions on a solid substrate, where a network of channels and reservoirs are present. By employing electric fields with electrically conducting liquids, volumes and/or ions can be moved from one site to another, different solutions formed by mixing liquids and/or ions, reactions performed, separations performed, and analyses carried out. In fact, in common parlance, the system has been referred to as "a laboratory on a chip." Various prior art devices of this type include U.S. Pat. Nos. 6,010,608, 6,010,607, 6,001,229, 5,858,195, and 5,858,187 which are a family of applications concerned with injection of sample solutions. See also, U.S. Pat. No. 5,599,432, European Pat. No. 0620432, international patent application no. WO 01/59440, and Verheggen et al., J. of Chromatography 452 (1988) 615–622.

In many of the operations, there is an interest in electrophoretically separating multiple sample components contained in dilute samples. For example, U.S. Patent Application Pub. No. 2002/0142329 describes a technique for performing assays for multiple target molecules using electrophoretic tag (e-tag) probes. The e-tag probes interact with a target, such as a single-stranded nucleic acid, a protein, a ligand-binding agent, such as an antibody or receptor, or an enzyme, e.g., as an enzyme substrate. The e-tag probes include a "portion" that binds to the target. After the target-binding portion of an e-tag probe binds to a target, a linking group of the electrophoretic probe is cleaved to release an "electrophoretic tag" that has a unique mass or charge-to-mass ratio, rendering such e-tags separable by, for example, electrophoretic separation on microfluidic devices.

Various processes are available for carrying out electrophoretic separations including but not limited to zone or capillary electrophoresis (CE) and isotachophoresis (ITP). Briefly, CE separations are performed in a capillary or channel filled with an electrophoretic medium under the influence of an electric field. Particles of different sizes and charges migrate along the channel at different speeds such that different components of a sample tend to separate spatially.

ITP processes are different than CE separations in that an ITP process stacks components of the sample between two electrolytes—a leading electrolyte and a trailing electrolyte. The components of the sample form bands between trailing and leading electrolytes. This phenomenon has been described in, e.g., Everaerts et al, Isotachophoresis. Theory, Instrumentation and Applications (Elsevier, Amsterdam, 1976); Burgi and Chien, chapter 16, in Landers, editor, Handbook of Capillary Electrophoresis, Second Edition (CRC Press, Boca Raton, 1997). See also international patent application no. WO 01/59440.

FIGS. 1A–1B illustrate an ITP separation. Referring to FIGS. 1A and 1B, a sample 58 containing components with different electrophoretic mobilities is placed between an electrolyte 60 with a leading edge ion and an electrolyte 62 containing a terminating or trailing-edge ion. These components may be placed in a capillary channel or tube, a section of which is shown at 56. The leading edge ion is a small ion, such as the chloride ion, having an electrophoretic mobility greater than that of any of the sample components. The counter-ion of the leading-edge ion is preferably chosen for its ability to buffer the solution.

Similarly, the trailing edge ion is one having an electrophoretic mobility lower than the slowest-migrating sample components. With the application of a voltage potential across the sample, sample components will band, by migration through the sample, until the fastest moving sample components are concentrated adjacent the leading-edge electrolyte and the slowest moving components, against the trailing edge electrolyte.

In the figures, the sample components to be separated are negatively charged, as are the leading- and trailing-ions, and the polarity of voltage is applied with the polarity shown, to attract the negatively charged components toward the right in the figures. Because the electric field across each section of the system is inversely proportional to the conductivity in that section, the section associated with the leading-edge ion is characterized by a relatively low electric field, and the section associated with the trailing-edge ion, with a relatively high electric field.

It is this different electric field or voltage gradient that maintains the sample components in a narrow band of sample components, each separated on the basis of their electrophoretic mobilities, once the sample components have stacked into a narrow band. Sample ions that diffuse back into the trailing electrolyte "speed up" under the higher electric field. Similarly, sample ions that diffuse forward into the leading electrolyte slow down under the lower electric field. At the same time, each sample component migrates to a position closely adjacent the sample components nearest in electrophoretic mobility, causing the components to stack into a tight sample band of separated components between the leading- and trailing-ion electrolytes.

Although each electrophoretic process affects the migration of the individual components of a sample, ITP can increase sensitivity by concentrating analytes. CE, on the other hand, though typically providing adequate sensitivity provides increased resolution of analytes having different mobilities.

U.S. Pat. App. 2002/0079223 describes an ITP-CE zone separation process. A combined ITP-CE separation process has attributes of each of the separation processes resulting in improved spatial separation between the analytes and improved efficiency. Briefly, as will be described further below, a combined ITP-CE separation first stacks the sample between the trailing edge electrolyte and the leading edge electrolyte to form component bands. Once the stack is formed, the stack is spatially separated along a channel to improve the spatial separation between the analytes.

In carrying out any of the above described electrophoretic separation processes on a microfluidic device, it is not surprising that voltage control is critical. Fluid and sample manipulation are controlled by application of voltages. However, accurately timing the application of voltages is fraught with difficulty since the timing depends on, amongst other things, the sample to be assayed. Indeed, the mobility of the sample ions is affected by a number of factors including, for example, viscosity of the liquids.

Various techniques for timing and application of voltages to drive the electrophoretic processes include a.) observing separation results and adjusting the timing and voltages based on the observed results and b.) visualizing dye concentrations under a microscope and adjusting the timing and voltages based on the microscope observations. Each of these techniques has marked drawbacks. Observation and analyzing separation results requires testing and optimization for each sample prior to commencing the actual testing. This is impractical.

Visualizing dye concentrations is also undesirable. Visualization of dye concentrations is undesirable because it is based on operator (human) observation. Activation of voltages or voltage switching is performed after a subjective observation of a microfluidic event such as, e.g., observing a stacked sample crossing a point along the channel. Human observation may be inaccurate and vary with time. Over long periods of time, for example, the observer's senses may deteriorate due to fatigue.

It is therefore desirable to provide an improved technique for controlling the application of voltages to carry out electrophoretic operations and other types of procedures on microfluidic devices. It is desirable to provide a technique that controls the voltages to drive electrophoretic separations on microfluidic devices and that does not suffer from the above mentioned drawbacks.

BRIEF SUMMARY OF THE INVENTION

A method for controlling an electric field in carrying out an electrokinetic process on a microfluidic device comprising 1.) applying an electric field to at least a first channel causing a sample to move towards a first location along the first channel; 2.) monitoring the first location for at least a portion of the sample; and 3.) automatically changing the electric field upon detecting the sample at the first location. The monitoring may be performed by optical detection such as light scatter, changes in refractive index, absorbance, fluorescence, such as laser-induced fluorescence (LIF), chemiluminescence, or another detection technique as is known to those of ordinary skill in the art. Additionally, a single point detector or an imaging detector, such as a charge coupled device (CCD), may be used to sense the sample.

The method may also include the step of monitoring additional locations. In performing operations when more than one location is monitored, a single optical detector may be employed to monitor the first and second locations. The single optical detector may be movable and may be positioned and repositioned at a new location as desired. Also, the single optical detector may comprise a relatively large (or otherwise directed) optical field such that multiple locations are observed from the single detector. Also, a plurality of optical detectors may separately monitor the plurality of locations.

In one embodiment of the present invention, the electrokinetic process is an ITP stacking process and the sample is electrophoretically stacked prior to reaching the first location. The step of automatically changing the electric field may comprise switching application of a voltage potential from a first set of reservoirs to a second set of reservoirs wherein the first and second sets of reservoirs are in fluid communication with the first channel. The ITP process may be automatically followed by a zone separation to spatially separate components of the sample.

In another embodiment of the present invention, the step of automatically changing the electric field upon detecting the presence of the sample at the first location is performed to inject a predetermined quantity of sample into a second channel. Accordingly, once the sample is sensed in this embodiment, a sample plug having a defined quantity may be injected into another portion of the channel network for further processing.

Another embodiment of the present invention is a method for performing an isotachophoresis stacking on a microfluidic device. The microfluidic device comprises a first, second, third, fourth and fifth reservoir and a first channel extending from the first reservoir to the fifth reservoir. The device further comprises a second channel, third channel, and fourth channel and the second channel, third channel and fourth channel are in fluid communication with the first channel at respectively second-channel, third-channel, and fourth-channel intersections. Each of the intersections are spaced along the first channel such that, relative to the first reservoir, the second-channel intersection is proximal to the third-channel intersection and the third-channel intersection is proximal to the fourth-channel intersection and the fourth-channel intersection is proximal to the fifth reservoir. Each of the second channel, third channel and fourth channel are in fluid communication with the second, third and fourth reservoirs respectively such that materials may be added and removed to the channels via the reservoirs. The steps of the method comprise 1.) applying a first voltage difference between the second reservoir and the third reservoir to move a sample from the second reservoir, into a sample region along the first channel and between the second-channel intersection and the third-channel intersection; 2.) applying a second voltage difference between the first reservoir and the second reservoir to drive a terminating electrolyte from the first reservoir towards the sample in the sample region; 3.) applying a third voltage difference between the first reservoir and the fifth reservoir to stack components of the sample between the terminating electrolyte and a leading electrolyte; and 4.) automatically applying a fourth voltage difference between the fourth reservoir and the fifth reservoir when the last component of the stacked sample reaches the fourth-channel intersection such that the components of the sample spatially separate as they move along the first channel towards the fifth reservoir.

The electric field may be applied using activated electrodes positioned in each of the reservoirs. Also, all electrodes need not be activated. Each of the electrodes may be variously activated and have varying voltages. The electric field strength is a function of a number of parameters such as the medium, the distance or length of the channel connecting the electrodes, the voltage difference between the electrodes, etc. Also, all reservoirs need not contain electrodes. One or more electrodes may be floated.

Another embodiment of the present invention is a controller configured to apply voltage differentials as recited in any one of the above methods.

Still another embodiment of the present invention includes a system comprising the above discussed controller and a detector adapted to sense when the sample reaches a location on the device. The detector may be positioned over the fourth-channel intersection. The detector may be an optical reader.

Still another embodiment of the present invention is a method for concentrating a plurality of components of a sample in a microfluidic device having a stacking channel and a separation channel downstream of the stacking channel, the method comprises: applying a first electric field to stack the components between a trailing electrolyte and a leading electrolyte along the stacking channel; and automatically applying a second electric field when at least a portion of the sample enters the separation channel whereby the components are further separated along the separation channel. The stacking channel and the separation channel may be portions of a main channel. Also, in one embodiment, the electric fields are applied by positioning and activating electrodes in reservoirs that are in fluid communication with the main channel. The electrodes may be permanent or removable from the reservoirs.

In another embodiment of the above method, the optical detector is positioned to monitor the separation channel for the presence of the sample and the first electric field is modified when the detector senses the sample.

BRIEF DESCRIPTION OF THE SEVERAL VIEWS OF THE DRAWINGS

FIGS. 1A–1B illustrate an isotachophoresis process in a microfluidic channel.

FIGS. 2A–2E illustrate application of voltage potentials to various reservoirs on a microfluidic device to carry out an isotachophoresis CE-zone separation process.

FIGS. 3A–3D illustrate application of voltage potentials to automatically inject a sample into another region of a microfluidic channel.

FIGS. 4a–4b show separation results of a sample separated on a microfluidic device using a closed-loop control ITP/zone electrophoresis process.

FIG. 5 shows results of multiple separations using a closed-loop control process.

FIG. 6 shows a detection system for optically monitoring a location on a microfluidic device.

DETAILED DESCRIPTION OF THE INVENTION

This is directed to electrophoretic separations performed on microfluidic devices and particularly, to automatically controlling electric fields used in carrying out isotachophoresis/zone electrophoresis separations.

FIGS. 2A–2E illustrate a technique for controlling application of voltages to perform an electrophoretic separation. In particular, FIGS. 2A–2E illustrate a closed-loop control technique for performing an ITP/CE zone procedure to separate components of a sample on a microfluidic device 2. The microfluidic device 2 shown in FIGS. 2A–2E includes a primary or main channel 4 fluidly connecting a first reservoir 10 and a second reservoir 20. The primary channel is shown in this figure as being straight but it need not be straight. Indeed, the primary channel may be curved, or a combination of straight and curved segments.

A plurality of branch channels are fluidly connected with the main channel. The branch channels are axially spaced along the main channel. As shown, branch channel 6 is most proximal to the first reservoir 10. Branch channel 8 is axially spaced a distance (d) from branch channel 6. Branch channel 8 is shown in an opposite or mirror position to branch channel 6 but it need not be so positioned. Further downstream of branch channel 8 is branch channel 12. The branch channels are shown at right angles to the first channel 4. However, the invention is not so limited and the branch channels may form angles (90 degrees or otherwise) with the first channel 4.

Also, branch channels 6, 8, and 12 are shown being fluidly connected to reservoirs 30, 40 and 50 respectively. As described in further detail below, the reservoirs provide ingress and egress openings for materials to be supplied or withdrawn. The reservoirs also are sites for the electrodes used in creating the electric fields. The electric fields electrokinetically drive the materials in the device. However, the materials may be driven using other means such as pressure means as is known to those of ordinary skill in the art.

Various techniques for fabricating microfluidic devices are described in the literature. See, for example, U.S. Pat. Nos. 6,176,962, 6,010,607, and 5,858,195; U.S. Pat. Pub. Nos. 2002/0079223 and 2002/0053399; and international application no. PCT/98/21869.

One fabrication technique is as follows: the channel network may be conventionally formed on a substrate or card, and covered by a transparent cover or film which is attached or bonded to the card conventionally. The substrate in which the channels are present will generally have a thickness of at least about 20 micrometers, more usually at least about 10 micrometers, usually not more than about 0.25 cm. The width of the substrate may be determined by the number of units to be accommodated and may be as small as about 2 mm and up to about 6 cm or more. The dimension in the other direction will generally be at least about 0.5 cm and perhaps, not more than about 50 cm, usually not more than about 20 cm.

The substrate may be a flexible film or relatively inflexible solid, where the microstructures, such as reservoirs and channels, may be provided by embossing, molding, machining, etc. The channel dimensions will generally be in the range of about 0.1 micrometers to 1 mm deep and about 0.5 micrometers to 1 mm wide, where the cross-section will generally be 0.1 $\mu m^2$ to about 1 $mm^2$. The channel lengths will vary widely depending on the operation for which the channel is to be used, generally being in the range of about 0.05 mm to 50 cm, more usually in the range of about 0.5 mm to 20 cm. The main and side channels may have the same or different cross-sectional areas, as well as the same or different shapes. The ratios of the lengths of the sample-loading region (e.g., between channel 6 and channel 8) and the separation region (e.g., between channel 12 and reservoir 20) is typically a selected ratio of 1:50 to 1:1.

The reservoirs will generally have volumes in the range of about 10 nl to 100 ⊠l; more usually have volumes in the range of about 500 nl to 10 $\mu l$. The reservoirs may be cylindrically shaped, conically shaped, or otherwise shaped. In some configurations, the reservoir is an uncovered portion of a channel.

The substrates and accompanying film will generally be plastic, particularly organic polymers. Examples of polymers that may be used alone or in combination with other polymers to form the substrate and film include polymers such as but not limited to acrylates, methacrylates, polyolefins, polystyrene, etc. or condensation polymers, such as polyethers, polyesters, polyamides, polyimides, dialkyl siloxanes, or norbornene (Zeonor-type) polymers, although glasses, silicon or other material may be employed. Desirably, the polymers will have low fluorescence inherently or can be made so by additives or bleaching, e.g. photobleaching.

A film will usually be placed over the substrate to at least enclose the channels, which film will usually have openings for communicating with the reservoirs and, where appropriate, introducing electrodes into the reservoirs. The enclosing film may be adhered to a substrate by any convenient means, such as thermal bonding, adhesives, ultrasonic welding, etc. The literature has many examples of adhering such films, see, for example, U.S. Pat. Nos. 4,558,333; and 5,500,071.

The control unit includes a power source or voltage sources which is operatively connected to the electrodes in the device. The power source is under the control of an electronic controller in the control device. Voltages may range from 10–6000 volts, or higher. Voltage potentials may range from 10–1000 volts/cm. The controller determines the sequence and timing of voltages applied to the electrodes, and the voltage levels. The operation and design of the controller, and in particular, the closed loop control of the voltages will be appreciated from the various processes described below.

Isotachophoresis/Zone Electrophoresis Separation

An ITP process requires a leading edge and a trailing edge electrolyte. Initially, the leading edge electrolyte 22 may be introduced into all the channels and the reservoirs. Examples of a leading edge electrolyte include ions of high mobility, such as chloride, acetate, or the like. Next, as shown in FIG. 2A, a sample 24 comprising a plurality of component species is loaded into reservoir 30. The sample is electrokinetically driven from reservoir 30 towards reservoir 40. For example, control unit 32 activates electrodes in reservoirs 30, 40 such that a voltage potential is applied across these reservoirs driving ions from reservoir 30 to reservoir 40. The sample may be driven from reservoir 30 by electrophoresis, differential pressure, a like technique, or another technique for driving sample from the reservoir as is known to those of ordinary skill in the art. The materials may be driven in bulk flow such as electroosmotic flow (EOF). The sample 24 is shown migrating along and occupying a region of the main channel 4 between the first branch channel 6 and the second branch channel 8. This sample region is a defined length (d) ranging from 100 µm to 10 cm, and more usually from 1 to 4 cm and perhaps between 150 to 250 microns. The width and depth of this channel segment may be the same as that described above.

Referring to FIG. 2B, a terminating edge electrolyte 26 may be added to reservoir 10 and migrated to the sample boundary of the sample region. Manipulating the terminating edge electrolyte 26 in this manner may be accomplished by applying a voltage difference between reservoirs 10 and reservoirs 30 while floating the other electrodes.

FIG. 2C illustrates injecting a plug of sample having a volume defined by the distance (d) discussed above. In particular, a voltage difference is applied between reservoirs 10 and 20. The other electrodes may be floated. That is, when not specifically controlled, the electrodes need not be activated. However, the invention is not so limited and all reservoir electrodes may be active to enhance (or compact) the shape or volume of the sample plug as is known to those of ordinary skill in the art.

As the voltage is applied across the main channel the trailing electrolyte 26, sample 28, and leading electrolyte 22 move downstream and the sample stacks between the leading electrolyte 22 and the trailing electrolyte 26. However, as discussed above, ITP stacking provides sample concentration, but does not provide spacing between component species. Accordingly, it may still be desirable to further separate the component species of the sample using a zone separation process.

As shown in FIG. 2D, a CE/zone separation may be commenced at the moment the stacked sample reaches (or passes) branch channel 12 (or the intersection of branch channel 12 with channel 4). In particular, an optical sensor or detector (D1) may be positioned along channel 4 such that it monitors a location along the main channel 4. Once a portion of the sample is sensed by the detector, the control unit immediately applies a voltage difference from reservoir 50 to reservoir 20 such that a leading edge electrolyte or another electrophoretic medium migrates into the main channel from reservoir 50. The leading edge electrolyte and the sample continue to migrate through the main channel towards the reservoir 20. The components of the sample spatially separate due to their electrophoretic mobilities and charges.

FIG. 2E illustrates separation of the components of the sample into spatially discrete segments 28A–28D along the main channel 4.

In one configuration of the present invention, the control unit is configured to automatically switch the voltages when a microfluidic event is detected such as detection of the presence of a sample at a location on the device. Automatic voltage application based on detection of the sample at certain locations eliminates human error which may arise from fatigue. Also, a closed loop system is more efficient than an open loop system because an open loop system requires observation and analysis of each sample prior to selecting the voltage-timing protocol. That is, in an open-loop control mode, testing must be performed prior to determining when the voltage potential should be switched from reservoirs 10–20 to reservoirs 50–20. In contrast, closed-loop control provides voltage switching in real time. A closed-loop system also eliminates operator subjectivity as to when a microfluidic event has occurred. Consequently, a closed loop control system is desirable in microfluidic ITP and zone separation processes.

The step of monitoring a location for the sample (or another microfluidic event) may be carried out using various mechanisms/techniques such as, for example, optical detection. Examples of optical detection include techniques such as light scatter, changes in refractive index, absorbance, fluorescence, such as laser-induced fluorescence (LIF), chemiluminescence, or other optical detection techniques as is known to those of ordinary skill in the art. Additionally, a single point detector or an imaging detector, such as a charge coupled device (CCD), may be used to sense the sample.

In the event LIF detection is employed to monitor a location, the laser may be directed normal to the plane of the microfabricated device, exciting molecules at or adjacent to a detection zone. In FIG. 6 is depicted a detection station 100. In conjunction with the detection station is a microfluidic chip 102, held in position by a quartz plate 104. The quartz plate may be part of a vacuum chuck, not shown, whereby the microfluidic chip 102 is held in fixed registry in relation to the detection station 100. Examples of other ways of maintaining the microfluidic chip in place include gravity, force pins, pressure, clips, reversible adhesives, etc. Also depicted is an electrode lid 106 with electrodes 108, where the electrodes 108 can extend into ports of the microfluidic chip 102, during operation of electrokinetic processes. As described above, the microfluidic chip 102 may have a plurality of channels instead of a sole channel. As shown, the detection station has optical housing 110, which may be a small tubular housing, which may be made of any convenient material, e.g., plastic, aluminum, steel, etc., and will desirably have the minimal dimensions necessary for housing the various components of the optical system. The optical system, to the extent permissible, can employ miniaturized optical elements, such as diffractive optical elements, DOEs. A single DOE may serve a plurality of functions, such as acting as a lens, mirror and/or grating, where the component may be about 3 mm×3 mm. The optical system 100 includes an aspherical lens 112 at one end of the housing in apposition to the channel in the microfluidic chip, which aspheric lens 112 directs the excitation beam to the center of the channel after appropriate orientation, as described below. An excitation light beam 114 is directed to dichroic mirror 116 or equivalent optical element by means of optical fiber connected to arm 120 of housing 110 by means of coupler 122. Light beam 114 passes through a lens 124, which serves to collect the divergent light from the fiber. The excitation beam 114 is then reflected by dichroic mirror 116, which reflects light of the excitation wavelength of interest and allows light outside the reflective wavelength to pass through the dichroic mirror. The internal walls and all supporting elements will desirably be black, so as to maximize scattered light absorption. The reflected light beam 126 is focused by aspherical lens 112 and forms a sharp small beam, which passes through the support plate 104 into channel 128. When fluorophore is in the channel 128, the fluorophores will be excited and emit light, which will exit the channel 128 and be collected by the aspherical lens 112. The emission beam may pass through the dichroic mirror 116, filter 132 to reject light outside the wavelength range of interest and lens 134 which focuses the light beam 130 on the entry of collection optical fiber 133. The optical fiber is attached to the housing 110 by means of coupler. The collection optical fiber 133 transfers the photons to a detector, not shown.

The housing 110 may be affixed to the orientation device 136 by means of flange 138. Flange 138 is bonded to and connects together as a movable unit housing 110, arm 120 and lever 140. Lever 140 is rotatably mounted on bearing 142, which is supported by axle 144. The orientation device 136 comprises a tubular casing 146, which is fixedly attached to an encoder unit 148 by L-bar 150. The casing 146 and motor unit 148 are held in fixed relationship, so that movement of the lever arm 140 can be accurately controlled and the position of the lever arm 140 and the housing 110 may be readily determined.

The encoder 148 is connected by connector 152 to the rod 154 on which cam 156 is fixedly mounted. Rod 154 passes through bearings 158 and 160, which are set in tubular casing 146, so as to maintain rod 154 in place and allow for rotation of cam 156 from a fixed axis of rotation. The tubular housing 146 has a fin 162 to which one end of a spring 164 is attached, being attached at the other end to lever arm 140. The spring 164 restrains lever arm 140 and urges the arm 140 in the direction of the fin 162 or in the counter-clockwise direction as indicated by broken line 166. Bar 168 is supported by bushings 170 and 172 and its length provides for a tight fit between the cam 156 and the contact position on lever arm 140. Therefore, the distance between the surface of the cam 156 on which the bar 168 is displaced and the lever arm 140 remains constant. As the cam 156 rotates, the bar 168 is extended or retracted in relation to the rod 154 on which the cam is journaled. As the lever arm 140 responds to the movement of the bar 168, the optical system in housing 110 scans the surface for the fluorescence being emitted.

The light source may be part of the moving optical train. Also, the light source may be divorced or separated from the moving optical train.

There may be a substantial drop at the borders of the channel 128 in the microfluidic chip 102. By knowing the position of the borders and the distance between the borders, the encoder can be controlled to move the bar 168 to center the housing 110 over the center of the channel 128. Once the housing is desirably positioned (e.g., centered over the channel), fluorescence may be monitored. The fluorescence intensity is directed by collection fiber 133 to a data collection and analysis device, not shown.

The microfluidic chip may be oriented so as to have a single channel within the confines of the width of a single housing so that the determination of the channel center is orthogonal to the channel. Alternatively, the channel may be at an angle to the path of the housing, so that the measurements are at an angle to the channel boundaries, still allowing for the center to be determined.

The optical detection and orientation system may have multiple light sources each emitting light at a different wavelength. Also, the optical detection and orientation system may have a multiple-wavelength light source, which may selectively emit light at different wavelengths. Examples of light sources may include, but are not limited to, the following: multiple-wavelength lasers, such as mixed-gas (argon and krypton) ion lasers, dye or multiple-dye lasers (pumped by either flashlamp or laser); an optical parametric oscillator (OPO) that is pumped by any uv laser, such as a frequency-quadrupled Nd:YAG laser; and pulsed xenon short-arc lamp in cooperation with a rapidly tunable optical filter, such as a small monochromator or a set of interference filters. Also, the light source may be adapted to deliver an expanded-beam having a diameter in the range of 2 to 50 mm. The light source may also be configured to deliver a fine or collimated beam having a diameter in the range of 0.1 to 2 mm.

Additionally, light reflecting structures may be removably submersed or permanently integrated within a chip to direct a beam across a detection zone. Such an approach may further utilize additional reflectors to allow light detection normal to the plane of the microfluidic device. The above detection schemes are meant for purposes of illustration. Other detection schemes may be employed in carrying out the present invention such as, e.g., the detection systems described in U.S. Pat. No. 6,399,952 filed May 12, 2000 and U.S. patent application Ser. No. 10/202,298 filed Jul. 23, 2002.

The detector(s) may also be used to detect the sample at multiple locations along the main channel 4. For example, as shown in FIG. 2E, a detector (D2) may be positioned at a second location along channel 4 to sense a microfluidic event or otherwise detect information. One or more detectors may thus be employed to detect the presence of a sample, to read the separated components of the sample, or to detect another microfluidic event. The information may be sent to a computer for analysis. Also, a single detector may monitor multiple locations. For example, a programmable controller may move either the detection system or the chip such that fluorescence at one or more locations is sequentially read. Additionally, an image of the entire chip, channel, or region may be recorded and analyzed to determine the signals at multiple locations simultaneously.

The above described process may be repeated as desired. It may be run in a high throughput manner wherein a cycle restarts upon detection of a microfluidic event. For instance, when a detector (D2) senses the last component in the sample, the control unit may be configured to activate the electrodes such that a new cycle is commenced. The new cycle may comprise the steps of sample loading, sample injection, and sample separation. The time to complete an entire cycle may range from 2 seconds to 1 hour and perhaps, 30 seconds to 180 seconds.

Closed-Loop Sample Injection

FIGS. 3A–3D illustrate another aspect of the present invention. In particular, FIGS. 3A–3D illustrate controlling voltages to inject a sample into another region of a microfluidic device for use in a chemical laboratory process such as an electrophoretic separation. FIGS. 3A–3D show an additional detector (D3) positioned along channel 8. Detector D3 is positioned such that it may sense (e.g., optically) the point, line or region where channel 8 branches from channel 4. Detector D3 is positioned such that it may detect materials entering channel 8 as soon as they enter channel 8. Various benefits and advantages arise from detecting the presence of the sample in channel 8 as will be apparent in view of the following example process.

Referring to FIG. 3A, a sample material 24 is loaded into reservoir 30. A voltage differential is applied between reservoir 30 and 40 creating an electric field that drives sample from reservoir 30 towards channel 4. As shown in FIG. 3B, the sample enters channel 4 and migrates towards channel 8. The other voltages may be floated. Also, the other reservoirs may have voltages associated therewith to actively control the shape (or compact) the sample plug or the liquids in the channels.

As shown in FIG. 3C, the sample eventually enters channel 8. As soon as the sample enters channel 8, a sample plug volume having a width and height defined by the cross section of channel 4 and a length equal to the distance between channels 6 and 8 may be sent downstream by switching the voltages from one set of reservoirs (reservoirs 30/40) to another set of reservoirs (reservoirs 10–20). Accordingly, a sample plug having a defined volume or quantity may be sent (e.g., injected) downstream. See, e.g., FIG. 3D.

The voltages may be switched automatically upon detector (D3) sensing a portion of sample 24 entering channel 8. The detector may be connected to a voltage control unit 32 which receives and analyzes signals from the detector. Based on the signal, the control unit determines whether or not to switch (change, supplement, etc.) the voltages from one set of reservoirs to another set of reservoirs. It is to be understood that a set of electrodes may include two or more electrodes.

Also, the detector and control unit may be set up such that only upon sensing the sample, a signal is delivered to the control unit. For example, in the event the detector is a fluorescent reader, the detector may be configured such that it provides an output signal only upon reading a fluorescent signal having a particular wavelength. Also, the invention is not limited to a control unit having a computer. Indeed, a control unit may be configured to be hardwired to provide voltage switching upon sensing the sample or another microfluidic event. For example, an optical reader may be provided that provides an output signal upon sensing a fluorescent material. The output signal may be delivered to a relay switch that automatically changes the voltage differentials to a different set of reservoirs. Typically, however, a controller will have (or communicate with) a computer or microprocessor that may read and/or evaluate a signal from the detector. If the signal from the detector is greater or less than a threshold value, the controller will switch the electric field. It is also to be understood, however, that other algorithms and methodologies may be used to determine when to switch, modify, or change electric fields.

To reiterate, when a portion of the sample 24 enters channel 8, the voltages may be automatically modified to send a controlled sample volume down channel 4 for further processing such as an ITP and CE zone separation. Also, by the term "modifying" an electric field, it is meant changing, switching, applying, or removing an electric field.

EXAMPLE

An ITP zone separation was performed on a microfluidic device using a closed-loop controller that automatically switched the voltages upon sensing a portion of a sample. The device was configured as shown in FIGS. 2A–2E.

A sample containing twelve different electrophoretic tag (eTag) reporters, each labeled with fluorescein, was added to the device and concentrated (or ITP stacked) as described in the text, above, corresponding to FIGS. 2A–2C. The concentrated sample was electrokinetically driven to detection point D1.

Detection point D1 was monitored using a photomultiplier tube (PMT) detector. The PMT detector collected the signal generated by laser induced fluorescence. An argon laser was directed at the detection point. The excitation wavelength was 488 nm. Emission was collected at 515–540 nm.

When the sample reached detector (D1), and the PMT detector recorded a large signal indicating that the sample had reached this detection point, the controller automatically modified the electric fields of the device to electrophoretically separate the concentrated sample along the separation channel (e.g., channel 4 of FIGS. 2A–2E). The detector was then repositioned to detection point D2 to monitor or measure the fluorescent signal at detection point D2. The distance between detection point D1 and detection point D2 was 4.4 cm.

FIG. 4A shows fluorescence vs. time at detection point D1 and detection point D2. As shown, a large fluorescent signal is recorded by detector D1 at about 75 seconds. This event triggers the controller to modify the electric fields.

FIG. 4B shows an enlarged view of the chart of FIG. 4A corresponding to detection point D2. Twelve peaks are shown corresponding to the twelve eTag reporters as they migrate past detection point D2. This data indicates that this microfluidic process efficiently separates the sample with good resolution.

FIG. 5 shows repeat separations of a sample using the closed-loop control scheme described above. A review of FIG. 5 indicates that this ITP/zone electrophoresis process is reproducible.

Although the devices described above typically include 5 reservoirs and a channel network connecting the reservoirs, the invention is not limited to the particular configurations shown. Indeed, more or less reservoirs may be provided and more or less channels and channel portions may be provided. Separate channel networks may be adjacent to one another on the same chip. Also, the control of voltages across the reservoirs may have applications other than the electrophoretic separations as described above. Automatic sensing and timing of voltages may be incorporated into a wide variety of microfluidic devices to carry out laboratory processes accurately and efficiently and without suffering the above mentioned drawbacks. Examples of microfluidic processes that automatic timing may benefit include, but are not limited to, reactions, mixings, heating, chemical sensing, injections, separations, washings, etc.

Although sensing the presence of a sample (or other material) has been described above with reference to optical configurations, sensing techniques are not so limited. Sensing may be performed by measuring a wide variety of properties or attributes including temperature, light, pressure, color, an electrical property (e.g., impedance), ultrasonic properties, etc. Once a microfluidic event is detected by the sensor/detector, an output signal may be sent to the controller or a relay switch to activate a secondary operation such as changing the voltage potential from one set of electrodes or reservoirs to another set of electrodes or reservoirs. Also, changing or modifying the voltage potential or differential between a set of electrodes may include a.) changing the voltage difference from one value to another greater or lower value as well as b.) floating the electrodes.

The microfluidic processes described above can lessen or eliminate subjective determination and analyses of microfluidic events. Consequently, errors in voltage timing can be reduced. This should improve CVs. Additionally, high throughput optimization may be carried out using automatic voltage control since fluid injections and separations, and entire cycles may be started/stopped based on highly sensitive detectors such as fluorescent readers.

All of the features disclosed in the specification (including any accompanying claims, abstract and drawings), and/or all of the steps of any method or process disclosed, may be combined in any combination, except combinations where at least some of such features and/or steps are mutually exclusive.

The invention is not restricted to the details of the foregoing embodiments. The invention extends to any one or combination of features as set forth in the claims.

All publications, patent applications, patents, and other references mentioned above are incorporated by reference in their entirety.

What is claimed is:

1. A method for performing an electrophoretic process on a microfluidic device comprising a first, second, third, fourth and fifth reservoir and a first channel extending from the first reservoir to the fifth reservoir, said device further comprising a second channel, third channel, and fourth channel and said second channel, third channel and fourth channel being in fluid communication with said first channel at respectively second-channel, third-channel, and fourth-channel intersections and each of said intersections being spaced along said first channel such that, relative to said first reservoir, said second-channel intersection is proximal to the third-channel intersection and the third-channel intersection is proximal to the fourth-channel intersection and the fourth-channel intersection is proximal to the fifth reservoir, and each of said second, third and fourth channels being in fluid communication with the second, third and fourth reservoirs respectively such that materials may be added and removed to the channels via the reservoirs, said method comprising:

applying a first voltage difference between the second reservoir and the third reservoir to move a sample from the second reservoir, into a sample region along the first channel and between the second-channel intersection and the third-channel intersection;

applying a second voltage difference between the first reservoir and the second reservoir to drive a terminating electrolyte from the first reservoir towards the sample in said sample region;

applying a third voltage difference between the first reservoir and the fifth reservoir to stack components of the sample between the terminating electrolyte and a leading electrolyte;

automatically applying a fourth voltage difference between the fourth reservoir and the fifth reservoir when the last component of the stacked sample reaches the fourth-channel intersection such that the components of the sample spatially separate while migrating along the first channel towards the fifth reservoir.

2. The method of claim 1 wherein an electrode is positioned in each of the reservoirs.

3. The method of claim 2 wherein at least one electrode is floated.

4. The method of claim 2 wherein all electrodes are simultaneously activated.

5. A system comprising the device as recited in claim 1 and a controller configured to apply voltage differentials as recited therein.

6. The system of claim 5 further comprising a detector adapted to sense when said sample reaches a location on said device.

7. The system of claim 6 wherein said location is said fourth-channel intersection.

8. The system of claim 6 wherein said detector is an optical detector.

9. The system of claim 6 wherein said detector senses at least one of fluorescence, absorbance, refractive index and light scattering from said sample.

10. A method for separating a plurality of components of a sample in a microfluidic device having a stacking channel and a separation channel downstream of said stacking channel, said method comprising:

applying a first electric field to concentrate the components between a trailing electrolyte and a first leading electrolyte along the stacking channel;

replacing at least a portion of the trailing electrolyte having the same composition as the first electrolyte; and applying a second electric field across the first leading electrolyte, the components and the second leading electrolyte when at least a portion of said sample enters said separation channel whereby the components are separated by electrophoretic mobilities along the separation channel.

11. The method of claim 10 wherein the stacking channel and the separation channel are portions of a main channel.

12. The method of claim 11 wherein said electric fields are applied by positioning and activating electrodes in reservoirs that are in fluid communication with said main channel.

13. The method of claim 12 wherein the electrodes are removable.

14. The method of claim 10 wherein an optical detector is positioned to monitor the separation channel for the sample and the first electric field is modified when the detector senses the sample.

15. The method of claim 14 said optical detector comprises a single point detector.

16. The method of claim 14 wherein said optical detector comprises an imaging detector.

17. The method of claim 16 wherein the imaging detector is a charge coupled device camera.

18. The method of claim 14 wherein said detector senses at least one of fluorescence, absorbance, refractive index and light scattering from said sample.

19. The method of claim 14 wherein said detector provides input to a control unit operated in closed loop mode.

* * * * *